United States Patent
Wang et al.

(10) Patent No.: US 7,309,309 B2
(45) Date of Patent: Dec. 18, 2007

(54) DYNAMIC AND STATIC MAGNETIC PULSE PHYSICAL THERAPEUTIC APPARATUS

(76) Inventors: Jian Wang, B-2, Building A, Century Garden Nan Men Wai Ave., Nan Ka District, Tianjin City (CN) 300100;
Jingyi Wang, B-2, Building A, Century Garden Nan Men Wai Ave., Nan Ka District, Tianjin City (CN) 300100

( * ) Notice: Subject to any disclaimer, the term of this patent is extended or adjusted under 35 U.S.C. 154(b) by 714 days.

(21) Appl. No.: 10/663,988

(22) Filed: Sep. 17, 2003

(65) Prior Publication Data
US 2004/0106842 A1 Jun. 3, 2004

(30) Foreign Application Priority Data
Sep. 25, 2002 (CN) .............................. 02 2 57421

(51) Int. Cl.
*A61N 2/00* (2006.01)
*A61N 1/00* (2006.01)
(52) U.S. Cl. .............................. 600/14; 600/10; 600/15
(58) Field of Classification Search ............... 600/9–15
See application file for complete search history.

(56) References Cited

U.S. PATENT DOCUMENTS
6,306,076 B1 * 10/2001 Gill ............................. 600/15

FOREIGN PATENT DOCUMENTS
CN 00120774.1 12/2000

\* cited by examiner

Primary Examiner—Samuel G Gilbert
(74) Attorney, Agent, or Firm—Nixon & Vanderhye P.C.

(57) ABSTRACT

Disclosed is a dynamic and static magnetic pulse physical therapeutic apparatus which can provide an energy superposition field of dynamic magnetic pulses including mechanical vibration, a pulse magnetic field, a permanent magnetic field, thermal radiation and far infrared radiation and an energy superposition field of static magnetic pulses including a pulse magnetic field, a permanent magnetic field, thermal radiation and far infrared radiation, individually or at the same time. It includes a shell, a far infrared radiation fin with a heating device, a plurality of annular permanent magnets and a control circuit; a dynamic magnetic pulse assembly or a static magnetic pulse assembly is provided at the center of the annular permanent magnet. The massage to the human body with a dynamic magnetic pulse energy field and a static magnetic pulse energy field of synchronous frequency makes the main and collateral channels of different parts of the human body receive synchronous massages of different forms and thus have obvious functions and improved curative effects on main and collateral channels deroppilation, activating blood and absorbing clots.

7 Claims, 2 Drawing Sheets

DYNAMIC AND STATIC MAGNETIC PULSE PHYSICAL THERAPEUTIC APPARATUS

TECHNICAL FIELD

The present invention relates to a physical therapeutic apparatus, and more particularly to a dynamic and static magnetic pulse physical therapeutic apparatus in which a dynamic magnetic pulse, a static magnetic pulse, a permanent magnetic field, and a far infrared radiation field are incorporated to accomplish physical therapy to the human body.

BACKGROUND OF THE INVENTION

At present, physical therapeutic apparatus utilizing mechanical vibration, a permanent magnetic field, a thermal radiation field and a far infrared radiation field to accomplish physical therapy to the human body has been widely used. For example, the Chinese patent application publication No. 00120774.1 discloses a dynamic magnetic pulse and far infrared physical therapeutic apparatus, which includes a shell, a far infrared heating fin beneath the panel inside the shell, a permanent magnet, a magnetic pulse assembly and a control circuit. The magnetic pulse assembly is installed at the center of the annular permanent magnet. The magnetic pulse assembly is a magnetic pulse vibration massage contact which comprises a solenoid with a projecting rabbet at the upper end, a columniform permanent magnet capable of moving up and down in the solenoid, a flexible cover at the rabbet of the solenoid with the spherical head of the flexible cover extended outside of the panel, a shock absorption pad provided at the upper and lower end surfaces of the annular permanent magnet and fixed beneath the panel; wherein the magnetization directions of the annular permanent magnet and the columniform permanent magnet are in parallel with the axis of the solenoid, perpendicular to the panel but in opposite directions. In this technology, the pulse current generated by the control circuit makes the solenoid generate a pulse magnetic field which makes the columniform permanent magnet of the magnetic pulse assembly move up and down, and thus massage action is generated in the form of mechanical vibration. Mechanical vibration, a magnetic field, a pulse magnetic field, a thermal radiation field and a far infrared radiation field are incorporated to form a superposition field of dynamic magnetic pulses to accomplish physical therapy to the human body.

In other physical therapeutic apparatus, a pulse magnetic field, a permanent magnetic field, a thermal radiation field and a far infrared radiation field are incorporated to form a superposition field of static magnetic pulses to accomplish physical therapy to the human body.

However, it is impossible to get an energy superposition field of dynamic magnetic pulses including mechanical vibration and an energy superposition field of static magnetic pulses including synchronous pulses at the same time to accomplish physical therapy to the human body.

SUMMARY OF THE INVENTION

The object of the present invention is to provide a dynamic and static magnetic pulse physical therapeutic apparatus which can provide an energy superposition field of dynamic magnetic pulses including mechanical vibration, a pulse magnetic field, a permanent magnetic field, thermal radiation and far infrared radiation and an energy superposition field of static magnetic pulses including a pulse magnetic field, a permanent magnetic field, thermal radiation and far infrared radiation, individually or at the same time.

The physical therapeutic apparatus of the present invention includes a shell, a far infrared radiation fin with a heating device, a plurality of annular permanent magnets and a control circuit; a dynamic magnetic pulse assembly or a static magnetic pulse assembly is provided at the center of the annular permanent magnet.

The dynamic magnetic pulse assembly comprises a solenoid, a columniform permanent magnet capable of moving up and down in the solenoid, and a flexible cover at the rabbet of the solenoid with the spherical head of the flexible cover extended outside of the panel; wherein the magnetization directions of the annular permanent magnet and the columniform permanent magnet are in parallel with the axis of the solenoid, perpendicular to the panel but in opposite directions. The static magnetic pulse assembly comprises a solenoid and an iron core in the solenoid.

The dynamic magnetic pulse assembly and the static magnetic pulse assembly may be used individually or at the same time.

When the dynamic magnetic pulse assembly is at rest, the columniform permanent magnet will suspend at the center of the annular permanent magnet according to the theory of magnetic repulsion between heteropoles because the magnetization directions of the columniform permanent magnet and the annular permanent magnet are in opposite directions. When the present invention is at work, the solenoid is galvanized with pulse current under the action of the control circuit. When the solenoid is galvanized, a pulse magnetic field is generated in the solenoid. The columniform permanent magnet can move up along the axis of the solenoid under the action of the pulse magnetic field. When the pulse electrical current is cut off, the columniform permanent magnet falls back to the original position along the axis of the solenoid. The reciprocating motion of the columniform permanent magnet generate mechanical vibration at the flexible cover. Therefore, the dynamic magnetic pulse assembly can produce a pulse magnetic field and mechanical vibration under the action of the pulse current.

Under the action of the control circuit, when the solenoid of the static magnetic pulse assembly is galvanized with a synchronous current with the solenoid of the dynamic magnetic pulse assembly, the solenoid and its iron core will produce a static pulse magnetic field with no mechanical vibration.

In the present invention, the dynamic magnetic pulse assembly and the static magnetic pulse assembly are incorporated, so that an superposition of dynamic pulses magnetic field including mechanical vibration, a pulse magnetic field, and a permanent magnetic field and an superposition field of synchronous static magnetic pulses including a pulse magnetic field and a permanent magnetic field. An energy superposition field of dynamic magnetic pulses and a synchronous energy superposition field of static magnetic pulses are generated incorporating the dynamic pulse magnetic field, the static pulse magnetic field far, the thermal radiation and the far infrared radiation generated by the far infrared radiation fin with a heating device, and the permanent magnetic field generated by the annular permanent magnet. The energy superposition field of dynamic magnetic pulses and the energy superposition field of static magnetic pulses can be used selectively in different cases.

Particularly, when the human body is massaged with the dynamic magnetic pulse energy field and the static magnetic pulse energy field of synchronous frequency at the same time, the main and collateral channels of different parts of the human body receive synchronous mechanical massage and pulse magnetic field massage, i.e. different parts of the human body receive synchronous massage of different forms and human body is regulated integrally. The apparatus of the present invention have obvious functions and improved curative effects on main and collateral channels deroppilation, activating blood and absorbing clots.

In summary, the dynamic and static magnetic pulse physical therapeutic apparatus of the present invention provide an energy superposition field of dynamic magnetic pulses including mechanical vibration, a pulse magnetic field, a permanent magnetic field, thermal radiation and far infrared radiation and an energy superposition field of static magnetic pulses including a pulse magnetic field, a permanent magnetic field, thermal radiation and far infrared radiation, individually or at the same time.

DETAILED DESCRIPTION OF THE PREFERRED EMBODIMENTS

Figure 1:
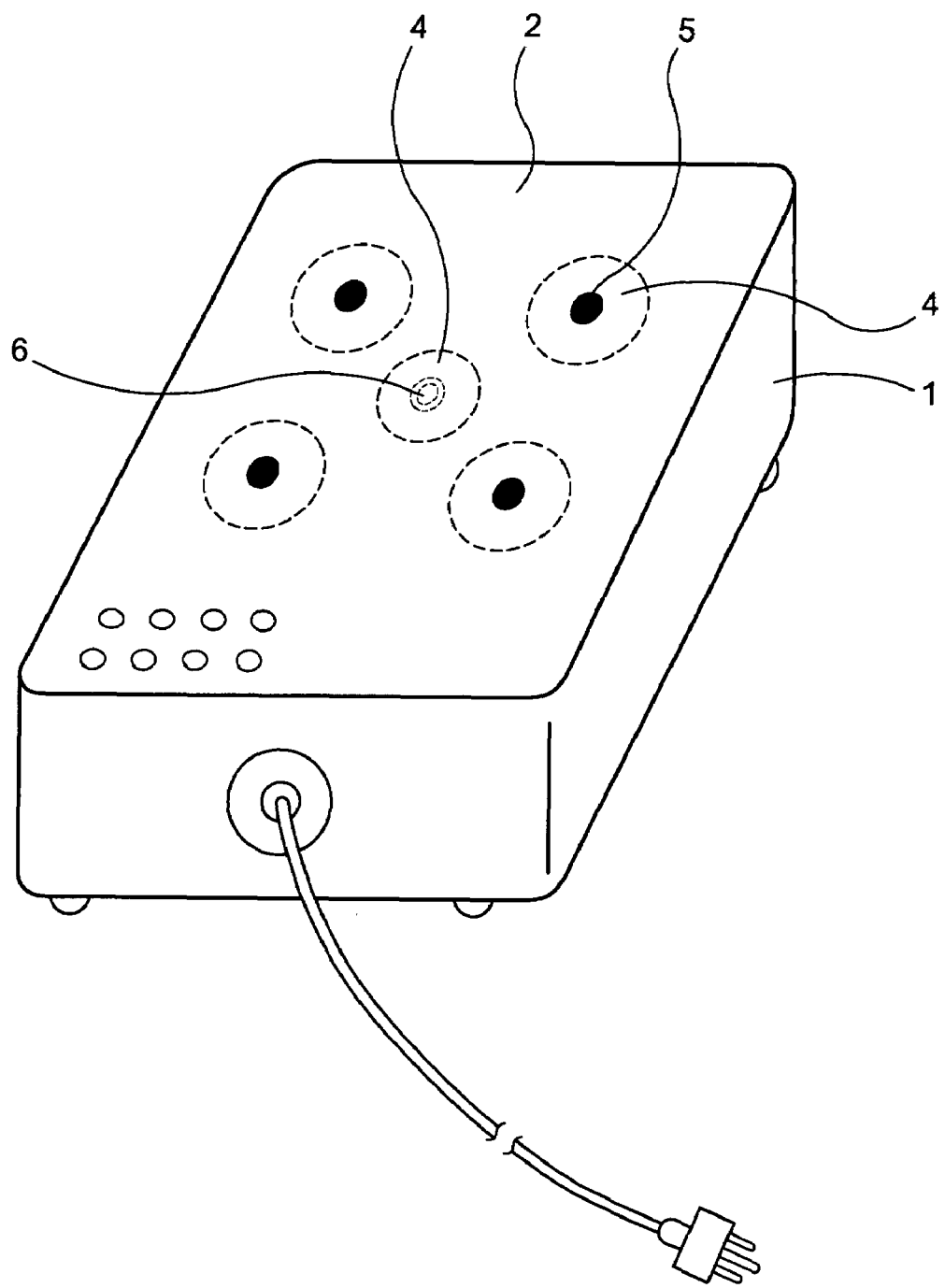
FIG. 1 is a perspective view of the apparatus according to the present invention.
Figure 2:
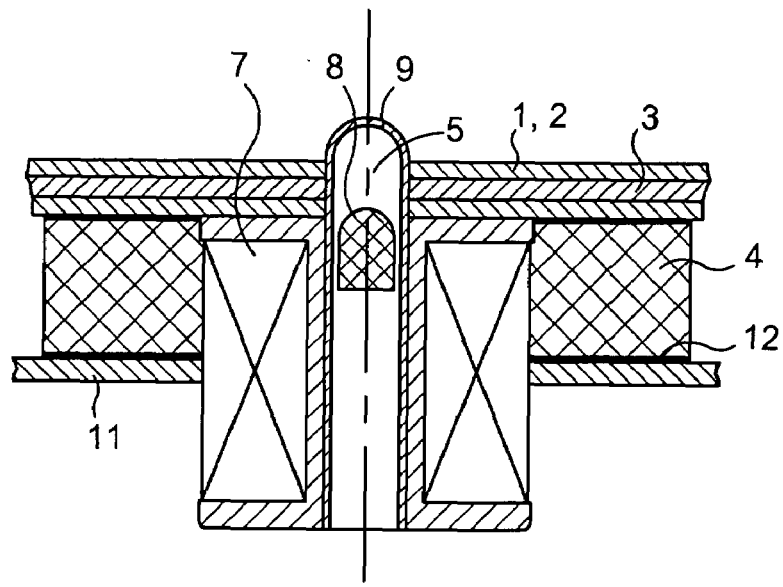
FIG. 2 illustrates a dynamic magnetic pulse assembly according to the present invention.
Figure 3:
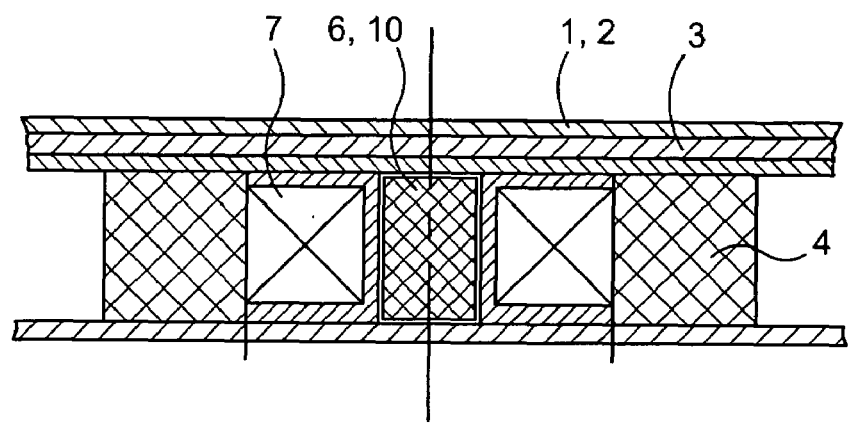
FIG. 3 illustrates a static magnetic pulse assembly according to the present invention In the drawings:
1—shell,
2—panel,
3—far infrared radiation fin with a heating device,
4—annular permanent magnet,
5—dynamic magnetic pulse assembly,
6—static magnetic pulse assembly,
7—solenoid,
8—columniform permanent magnet,
9—flexible cover,
10—iron core,
11—yoke, and
12—shock absorbing pad.

In a preferred embodiment of the present invention, the apparatus comprises a shell 1, a far infrared radiation fin with a heating device 3, five annular permanent magnets 4 and a control circuit. The shell 1 was a rectangular box made of plastic material. A panel 2 was the upper layer of the shell 1. The far infrared radiation fin with a heating device was set beneath the panel 2. The annular permanent magnet 4 was fixed on the yoke 11 with an iron stand. The shock absorbing pad 12 was installed between the annular permanent magnet 4 and the yoke 11. Among the five the annular permanent magnets 4, one static magnetic pulse assembly 6 was put at the center of the panel 2 and four dynamic magnetic pulse assemblies 5 were put in the peripheral of the panel.

When the apparatus of the present invention is used for the physical therapy treatment of the abdomen of the human body, the four dynamic magnetic pulse assemblies were put in the peripheral the abdomen and the static magnetic pulse assembly was put on the navel. The clinic has proved that the combination of the dynamic magnetic pulse assemblies and the static magnetic pulse assembly can produce better curative effect.

The dynamic magnetic assemblies or the static magnetic assembly can also be used individually.

What is claimed is:

1. A dynamic and static magnetic pulse physical therapeutic apparatus, including a shell, a far infrared radiation fin with a heating device, a plurality of annular permanent magnets and a control circuit; further comprising a dynamic magnetic pulse assembly and a static magnetic pulse assembly that may be used individually or at the same time.

2. The apparatus according to claim 1, wherein a total of five annular permanent magnets is provided with one in each of four corners and one in a center of the shell, and the dynamic magnetic pulse assembly is provided at the center of each of the annular permanent magnets in each corner of the shell and the static magnetic pulse assembly is provided at the center of the annular permanent magnet in the center of the shell.

3. The apparatus according to claim 1, wherein either the static or dynamic magnetic pulse assembly is provided at the center of each of the annular permanent magnets.

4. A dynamic and static magnetic pulse physical therapeutic apparatus, comprising:
    a shell;
    a total of five annular permanent magnets provided with one in each of four corners and and one at a center of the shell,
    a dynamic magnetic pulse assembly provided at a center of each of the annular permanent magnets at the four corners of the shell, and
    a static magnetic pulse assembly provided at the center of the annular permanent magnet at the center of the shell.

5. A magnetic pulse physical therapeutic apparatus, including a shell, a far infrared radiation fin with a heating device, a plurality of annular permanent magnets, a control circuit, and a static magnetic pulse assembly provided at the center of each of the annular permanent magnets.

6. The apparatus according to claim 5, further comprising a dynamic magnetic pulse assembly.

7. The apparatus according to claim 6, wherein the static and dynamic magnetic pulse assemblies are operable individually or in unison.

* * * * *